United States Patent [19]

Knowles et al.

[11] Patent Number: 5,789,158
[45] Date of Patent: Aug. 4, 1998

[54] DEVELOPMENTAL EMBRYONIC MOUSE CDNA LIBRARIES

[75] Inventors: Barbara B. Knowles, West Chester; Jay L. Rothstein, Bensalem; Dabney Johnson, Philadelphia, all of Pa.; Davor Solter, Freiburg, Germany

[73] Assignee: The Wistar Institute of Anatomy and Biology, Philadelphia, Pa.

[21] Appl. No.: 439,410

[22] Filed: May 18, 1995

Related U.S. Application Data

[63] Continuation of Ser. No. 906,838, Jun. 30, 1992, abandoned.

[51] Int. Cl.$^6$ .............................. C12Q 1/68; C07H 21/02
[52] U.S. Cl. .................................... 435/6; 536/23.1
[58] Field of Search ........................ 935/56, 77, 78; 536/23.1

[56] References Cited

FOREIGN PATENT DOCUMENTS

| | | |
|---|---|---|
| 0154186 | 9/1985 | European Pat. Off. . |
| 0242991 | 10/1987 | European Pat. Off. . |
| 0354624 | 2/1990 | European Pat. Off. . |
| WO91/17271 | 11/1991 | WIPO . |

OTHER PUBLICATIONS

J Rothstein et al., "Gene Expression During Preimplantation Mouse Development", *Genes and Development*, 6(7) :1190–1201 (Jul., 1992) [Rothstein I].

J. Rothenstein et al., "Murine Preimplantation cDNA Libraries: Characterization, Analysis and Cytokine Growth Factor Expression", Abstract and poster presented at the *1991 meeting on Mouse Molecular Genetics*, (Heidelburg, Germany) (Aug. 21–25, 1991) [Rothstein II].

N. Telford et al., "Transition from Maternal to Embryonic Control in Early Mammalian Development: A Comparison of Several Species", *Molec. Reprod. Dev.*, 26:90–100 (1990).

G. Shultz, "Utilization of Genetic Information in the Preimplantation Mouse Embryo", in *Experimental Approaches to Mammalian Embryonic Development*, ed. J. Rossant and R. A. Pedersen, pp. 239–265 (1986).

D. Rappolee et al., "Developmental Expression of PDGF, TGF-a, and TGF-b Genes in Preimplantation Mouse Embryos", *Science*, 241:1823–1825 (Sep., 1988).

K. Taylor et al., "Patterns of mRNA Prevalence and Expression of B1 and B2 Transcripts in Early Mouse Embryos", *Development*, 101:877–892 (1987).

D. Weng et al., "Estimates of mRNA Abundance in the Mouse Blastocyst based on cDNA Library Analysis", *Mol. Repro. Dev.*, 1:233–241 (1989).

M. Ko, "An Equalized cDNA Library by the Reassociation of Short Double-Stranded cDNAs", *Nucleic Acids Res.*, 18(19) :5705–5711 (1990).

J. Short et al., "Lambda ZAP: A Bacteriophage lambda Expression Vector with in vivo Excision Properties", *Nucl. Acids Res.*, 16(15) : 7583–7600 (1988).

Maniatis et al., "Construction and Analysis of cDNA Libraries", *Molecular Cloning, A Laboratory Manual*, 2nd ed., pp. 8.3–8.9 (1989).

J. McConnell et al., "Construction of a Representative cDNA Library from mRNA Isolated from Mouse Oocytes", *FEBS*, 195(1,2) :199–202 ( Jan., 1986).

H. Sive et al., "A Simple Subtractive Hybridization Technique Employing Photoactivatable Biotin and Phenol Extraction", *Nucl. Acids Res.*, 16(22) :10937 (1988).

D. Giebelhaus et al., "Changes in the Quantity of Histone and Actin Messenger RNA During the Development of Preimplantation Mouse Embryos", *Devel. Biol.*, 98:148–154 (1983).

M Noziaki et al., "Isolation of Endo A cDNA from Mouse 8–Cell Stage Embryos", *Biochem. Biophy. Res. Comm.*, 154(3) :890–894 (Aug., 1988).

J. Fargnoli et al., "Low–Ratio Hybridization Subtraction", *Analy. Biochem.*, 187:364–373 (1990).

Belansky et al, Nucleic Acid Res. 17: 2919–2933 (1989).

Kriegler "Gene transfer and Expression", p. 27, 1990.

*Primary Examiner*—Eggerton A. Campbell
*Attorney, Agent, or Firm*—Howson and Howson

[57] ABSTRACT

The present invention provides a number of cDNA libraries constructed from unfertilized eggs and 2-cell, 8-cell and blastocyst stage embryos, as well as a number of novel genes expressed in the 2-cell libraries.

7 Claims, 2 Drawing Sheets

DEVELOPMENTAL EMBRYONIC MOUSE CDNA LIBRARIES

This is a continuation of U.S. patent application Ser. No. 07/906,838 filed on Jun. 30, 1992 abandoned.

This work was made with support from the National Institutes of Health Grant Nos. CA10815, CA18470, HD21335, and T32-CA09140. The United States government has certain rights in this invention.

FIELD OF THE INVENTION

This invention relates generally to the field of DNA libraries, and more specifically to mammalian embryonic libraries.

BACKGROUND OF THE INVENTION

The molecular control of mammalian preimplantation embryogenesis remains largely unexplored, due, in large part, to the difficulty of obtaining sufficient quantities of timed embryos for experimentation. Nonetheless, knowledge about the changes in gene expression which underlie this period is essential to understanding mammalian development. Several lines of evidence, most notably, that inhibition of transcription at the 1-cell stage blocks protein synthesis and all subsequent development after the first cleavage division, coupled with the finding that initiation of synthesis of all classes of RNA occurs at the 2-cell stage, point to the early activation of the embryonic genome [Telford et al. *Molec. Reprod. Dev.*, 26:90–100 (1990)]. Temporal changes in transcription are also likely to herald the completion of cleavage and the formation of first differentiation cells, those of the trophectoderm [G. A. Schultz, "Utilization of genetic information in the preimplantation mouse embryo," in *Experimental approaches to mammalian embryonic development*, ed. J. Rossant and R. A. Pedersen, pp. 239–265, Cambridge University Press, Cambridge (1986)].

One approach to identifying genes of relevance to mammalian development has been to investigate those genes with sequence homology to genes of developmental importance in other vertebrate or invertebrate organisms. However, considering that early development in mammals results in an implantation-competent embryo, it is likely that the genes which control this process are unique to the mammalian embryo. All of these considerations have motivated several investigators to attempt to identify genes expressed in these early mammalian development stages.

The polymerase chain reaction (PCR) has been applied to study genes expressed during this period, thus circumventing the problem of obtaining sufficient embryonic material for study [Rappolee et al, *Science*, 241:1823–1825 (1988)]. The drawback to this technique is that only transcripts of known genes can be readily identified. Classically, cDNA libraries have provided a useful resource for identifying novel genes transcribed in specific cell types or tissues. Indeed, attempts to prepare cDNA libraries from unfertilized eggs or single stages of preimplantation embryo have been made [Taylor and Piko, *Development*, 101:877–892 (1987); Weng et al, *Mol. Repro. Dev.*, 1:233–241 (1989), Ko, *Nucleic Acids Res.*, 18:5705–5710 (1990)]. Yet for technical reasons, none of these attempts have provided reliable sources for the comprehensive analysis of genes differentially expressed during early embryonic development.

There exists a need in the art for reliable sources of sufficient quantities of timed mammalian embryos for the identification and isolation of genes in early mammalian development and for use in assaying the efficacy of various therapeutic agents.

SUMMARY OF THE INVENTION

In one aspect the present invention provides a novel mouse embryonic cDNA library derived from the unfertilized egg stage of cellular division (UESL).

In another aspect, the present invention provides a novel mouse embryonic cDNA library derived from the 2-cell stage (2CSL) of cellular division.

In yet another aspect, the present invention provides a novel mouse embryonic cDNA library derived from the 8-cell stage (8CSL) of cellular division.

In still another aspect, the present invention provides a novel mouse embryonic cDNA library derived from the blastocyst stage (BSL) of cellular division.

The invention further provides two specialized subtractive libraries which have been prepared from the 2CSL. These 2-cell subtractive libraries have been designated 2CSL-I and 2CSL-II.

In still another aspect, the present invention provides a method of screening the novel libraries of the invention for novel genes, growth factors and signals which mediate changes resulting in embryonic cell differentiation or proliferation.

Other aspects and advantages of the present invention are described further in the following detailed description of the preferred embodiments thereof.

DETAILED DESCRIPTION OF THE INVENTION

Figure 1:
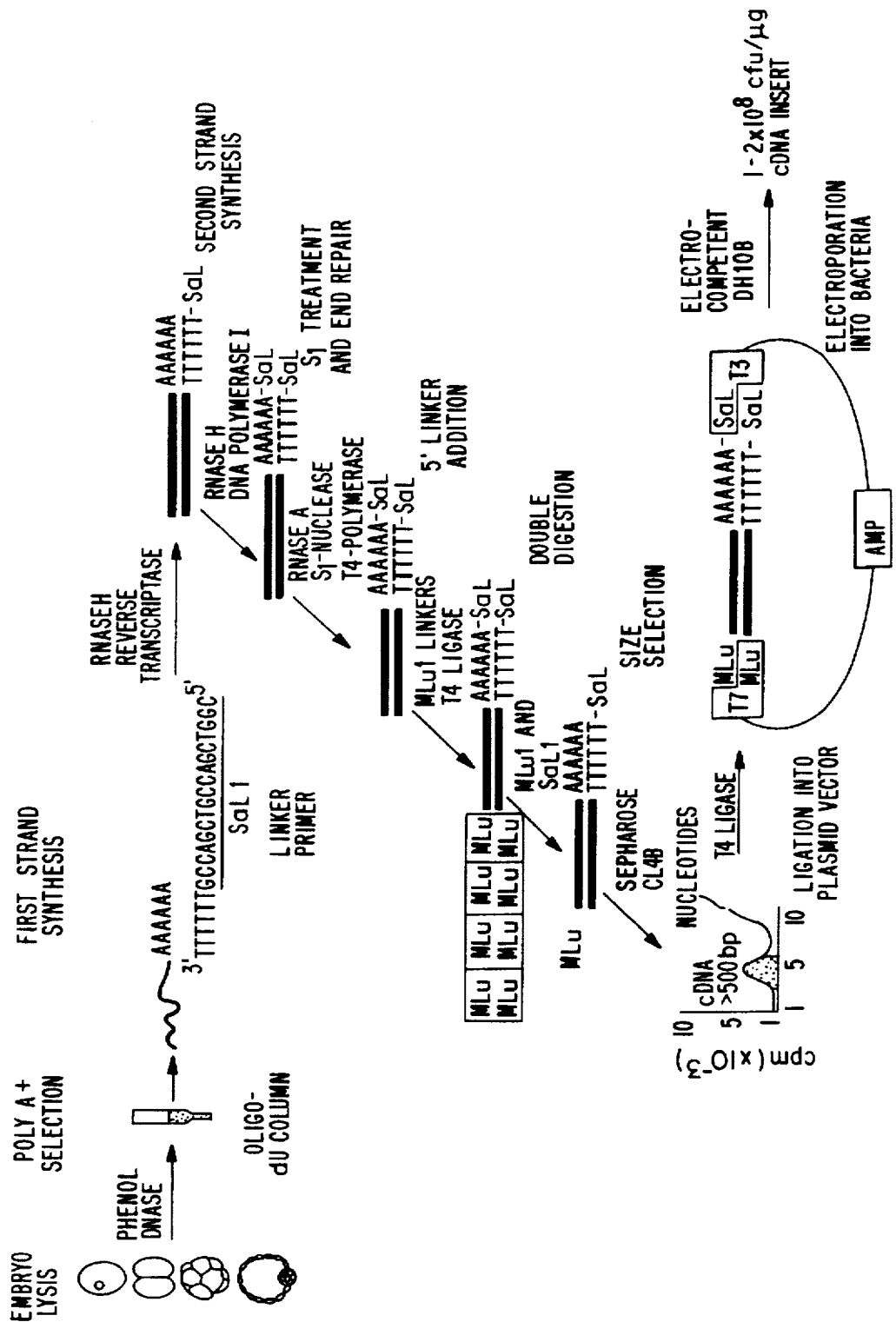
FIG. 1 is a schematic which illustrates the scheme for synthesis of the embryonic cDNA libraries.
Figure 2:
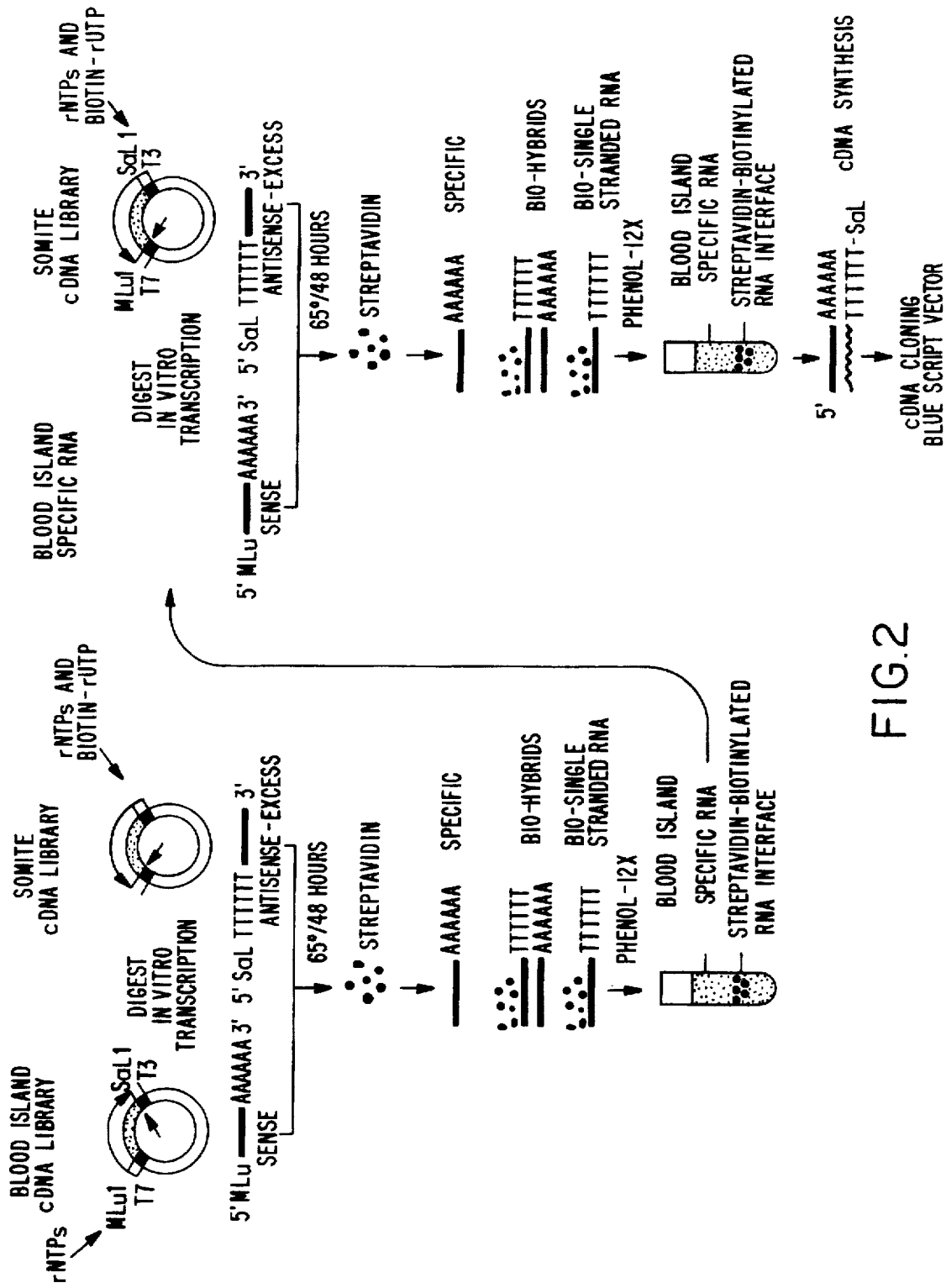
FIG. 2 is a schematic which illustrates the scheme for the generation of primary subtractive cDNA libraries (2CSL-I).

The present invention provides mammalian unfertilized egg and embryonic stage-specific cDNA libraries, which are a unique resource for the identification and isolation of genes expressed in the early mammalian embryo and prospective reagents for assays. The embryonic stage-specific cDNA libraries include a 2-cell stage library (2CSL), an 8-stage library (8CSL) and a blastocyst-stage library (BSL). The existence of these novel libraries provides an essential resource which does not violate the existing bans on human fetal research, and which may eliminate the use of animals in such research.

These libraries provide a source of cells which are useful for research, particularly relating to in vitro fertilization or pre-implantation (14 days old or younger), thus eliminating the need for fetal tissue. Further, the libraries of the invention provide a source of novel genes which are expressed in the early stages of development. These genes may provide insights into early pregnancy loss, i.e., the genes or antibodies to these genes may provide a marker for early pregnancy loss or act as a diagnostic agent therefor. Alternatively, these libraries and genes contained therein provide agents capable of controlling cell growth and differentiation.

As described in detail in Example 1 below, these libraries were obtained from B6D2/F mice, mated to D6D2 males, where appropriate. cDNA library construction was performed by modifying current cDNA cloning and electroporation protocols thus enabling high transformation efficiency of cDNA. Emphasis on high cloning efficiency was essential for high representation of genes expressed from the preimplantation embryo and their ultimate isolation by direct or subtractive hybridization methods. In this regard, a cDNA cloning strategy was established that allowed the efficient cloning of 10–100 ng mRNA since the mouse embryo contains no more than 50 pg of poly (A3+) mRNA at any stage of preimplantation development. This amount of mRNA would require the collection of 5–10,000 embryos for each stage, in order to obtain enough mRNA to make libraries using current methods. To obtain a representative library, inclusive of rare transcripts, the size of the library should be at least $10^6$ clones. Since the average percent conversion of mRNA to single stranded cDNA was observed to be 20–40%, the cloning efficiency for such a library needs to be nearly $2\times10^8$ cfu/µg cDNA.

Until now, few methods existed that provided directional cloning of cDNA into plasmids with these high efficiencies. Although λ cloning strategies exist, such as, λgt or λZAP, the phage packaging reactions can vary greatly from one to the other, and thus these methods fail to guarantee very high cloning efficiencies. Additionally, λ methods cloning require the manipulation of large vector arms, rarely allowing directional cloning and thus make direct subtractive hybridization difficult. Although λ cloning systems are available that provide a means to convert the libraries to single-stranded or double stranded plasmids, thus offering a way to avoid the problems associated with the vector arms, this method is not efficient and requires an added conversion step where efficiency is less than 100%. The advent of electroporation methods for the introduction of nucleic acid into bacteria has made possible the use of standard plasmid vectors for high efficiency cDNA cloning [Hanahan et al, *Methods Enzymol.*, 204:63 (1991)].

The libraries of the invention have been deposited with the American Type Culture Collection, 12301 Parklawn Drive, Rockville, Md. 20852, USA for patent purposes. Upon notification of issuance of this application, or to comply with requirements for foreign filing, these restrictions will be removed. The ATCC accession numbers of these libraries are as follows. The UESL has ATCC #69022, and was deposited on Jun. 30, 1992; the 2CSL has ATCC #69027, and was deposited on Jun. 30, 1992; the 8CSL has ATCC #69024, and was deposited on Jun. 30, 1992; the BSL has ATCC #69026, and was deposited on Jun. 30, 1992.

These libraries provide an excellent source for screening cells at the early stages of development for novel genes, gene fragments, or other nucleotide sequences encoding proteins which are implicated in the differentiation and/or proliferation of cells. As described below, plasmid vectors are currently available that can accommodate the directional cloning of cDNA such that T7 and T3 RNA polymerase promoter sequences can be used to generate sense and antisense transcripts for subtractive hybridization and riboprobe synthesis.

Thus, the present invention provides a method of identifying a gene or gene fragment contained within a library of the invention. This method involves the synthesis of at least one unique DNA probe sequence comprising a DNA sequence homologous to at least one DNA sequence within a selected gene or gene fragment, and of a size to stably hybridize to that gene or fragment thereof. The DNA probe is labeled and hybridized to the library of the invention. This label permits the identification of the gene or gene fragment. For example, a probe may be used to identify and amplify, e.g., by polymerase chain reaction (PCR), a nucleotide sequence which encodes a protein of interest.

Any polynucleotide sequence used as a probe and capable of hybridizing to the mammalian embryonic libraries of the invention under stringent hybridization conditions [see, Sambrook et al, *Molecular Cloning (A Laboratory Manual)*, 2d edit., Cold Spring Harbor Laboratory (1989), pages 387 to 389] to the DNA sequences of the invention is also covered by this invention. An example of one such stringent hybridization condition is hybridization at 4×SSC at 65° C., followed by a washing in 0.1×SSC at 65° C. for an hour. Alternatively, another stringent hybridization is in 50% formamide, 4×SSC at 42° C.

DNA sequences which hybridize to the sequences of the invention under less stringent hybridization conditions are also encompassed within this invention. Examples of such low-stringency hybridization conditions are 4×SSC at 50° C. or hybridization with 30–40% formamide at 42° C.

Screening techniques other than PCR or hybridization are well known to those of skill in the art and the selection of the techniques does not limit the present invention. The procedures for isolating and identifying gene fragments are well known to those of skill in the art [see, e.g. T. Maniatis et al, *Molecular Cloning (A Laboratory Manual)*, Cold Spring Harbor Laboratory (1982)].

Once identified and sequenced, the nucleotide fragments of the genes of the invention may be readily synthesized by conventional means, e.g. Merrifield synthesis [Merrifield, *J.A.C.S.*, 85:2149–2154 (1963)]. Alternatively, the DNA may be produced by recombinant methods, then sequenced. Cloning procedures are conventional and are described by T. Maniatis et al, *Molecular Cloning (A Laboratory Manual)*, Cold Spring Harbor Laboratory (1982).

Further, this method can be performed using known probes in order to determine whether or not a selected gene is expressed at a stage represented by one or more of the libraries of the invention. Genes for which the libraries are likely to be probed include, for example, growth factors and transcription factors.

As described in the examples below, to date, the results obtained by probing these libraries with single copy genes, such as intracisternal A-type particle (IAP), tissue plasminogen activator (t-PA), B1/B2 repeats and the like, indicates that they are representative of genes reported to be transcribed at these stages of cellular development. The estimation of actin levels made in the examples below should resolve the controversy over the quantity of actin message in the preimplantation embryo. Previously, estimates of actin mRNA abundance were made by comparing the level of embryonic actin mRNA to that in mRNA from a non-embryonic standard source, a technique subject to variation. Quantitation of independent actin clones in cDNA libraries overcomes this limitation.

A difference has been detected between B1 and B2 transcript levels in the unfertilized egg and 2-cell stage libraries on the one hand, and the 8-cell and blastocyst stage libraries on the other. Previous studies of total unfractionated RNA revealed an increase in B1 and B2 repeat-containing transcripts throughout preimplantation development [(Taylor and Piko et al, Development, 101:877–892 (1987); Poznanski and Calarco, Dev. Biol., 143:271–281 (1991)]. The frequency of B1 and B2 repeat-containing cDNAs decreases in the libraries of the present invention after the 2-cell stage. Changes in the RNA polymerase II and III activity in the embryo after the activation of the embryonic genome at the 2-cell stage may be responsible for this difference. Previous studies have suggested that changes occur in the relative amounts of RNA polymerase II and III activity between the 8-cell stage and blastocyst, the earliest embryonic stages investigated [Warner, "RNA polymerase activity in preimplantation mammalian embryos," in *Development in mammals*, ed. M. H. Johnson, pp. 99–136, Elsevier/North-Holland, New York (1977)].

The mammalian embryonic cell cDNA libraries of the invention provide a screening tool for the polyadenylated transcripts present in the various stages of development. Interactions of polypeptide growth factors with their receptors provide signals which mediate changes in gene expression resulting in differentiation or proliferation. The inventors, because of the novel libraries provided herein, have found evidence for the differential expression of several differential-inducing cytokines in the early embryo. Moreover, IL-7 transcripts, a factor known to induce the differentiation of immature lymphocytes [Henney, *Immunol. Today*, 10:170–173 (1989)] and to directly activate n-myc and c-myc in pre-B cells [Morrow et al, *Genes and Dev.*, 6:61–70 (1992)], has been identified in the unfertilized egg library of this invention. Transcription of IL-6, which is known to induce expression of several other genes including IL-1 [Lotem et al, *Cell Growth Differ.*, 2:421–427 (1991)] is found by the 8-cell stage. IL-1β, a pleiotropic differentiative factor capable of inducing the expression of other genes [Oppenheim et al, Immunol. Today, 7:45-56 (1986)], has been identified in the blastocyst library. IL-1 has been detected in the trophoblast and placental tissue of murine embryos and later stage human fetuses [Flynn et al, *Science*, 218:475–476 (1982); Crainie et al, *Biol. Reprod.*, 43:999–1005 (1990); Masuhiro et al, *J. Clin. Endocrinol. Metab.*, 72:594–601 (1991), and Taniguchi et al, *J. Obstet. Gynecol.*, 165:131–137 (1991)], suggesting that the trophectoderm of the blastocyst, the first differentiated cell type of the embryo, may be the cell type in the blastocyst responsible for the observed IL-1β expression. Transcription of IFN-γ, previously established as a product of T lymphocytes which provides an inductive signal to change gene expression, has been found at the blastocyst level. Thus, exploration of these libraries with probes of known genes indicates that these factors are sequentially transcribed prior to and at the time of the formation of the first differentiated cell type in the embryo.

Since each cDNA library of the invention is representative, it is expected to contain at least one cDNA clone of most of the genes transcribed in the corresponding stage in the mouse. Thus, by using probes derived from known genes and new probes isolated by such techniques as subtraction, these libraries provide the much needed instrument to determine whether the genes transcribed at the two cell stage are independently activated to perform a stage-specific function or if most of the embryonic genome is transcriptionally activated at the 2-cell stage and then, on differentiation, enhanced expression or specific repression of specific gene subsets occurs.

Thus, the present invention also provides a method of generating specialized subtractive cDNA libraries which provide access to mammalian genes expressed at a predetermined temporal or spatial coordinate. These specialized libraries may also be useful in identifying and isolating cellular activities and the genes responsible for these activities early in mammalian development.

Such specialized subtractive libraries can be prepared as described in Example 4 below. Briefly, the subtraction technique described herein takes advantage of the high binding affinity of biotin with avidin or streptavidin [Sive and St. John, *Nucleic Acids. Res.*, 206:467 (1988)]. In this method biotin molecules are incorporated into one of the two hybridizing strands (antisense) and the other (sense) is either labeled with $^{32}$P-dCTP or left cold. The resulting transcripts are hybridized and treated with streptavidin and the separation of unique sense strands is made by phenol extraction which will partition all single stranded antisense and hybrid molecules into the organic phase and leaving unique sense strands in the aqueous phase.

The embryonic cDNA libraries of the invention serve as the starting point for the generation of a series of subtraction libraries enabling identification and isolation of stage-specific genes. For example, if genes and gene fragments from the 8-cell stage are desired, a subtractive library can be prepared from the mammalian embryonic libraries of the invention by the methods described above. The novel gene and/or gene fragments are then identified by synthesizing a DNA probe comprising a DNA sequence homogologous to a DNA sequence of the 8CSL, labeling the DNA probe, hybridizing the labeled DNA probe to the 8CSL, the label permitting the identification of the gene or gene fragment. Similar techniques can be used to identify genes and gene fragments from the other mammalian embryonic cell lines of the invention. Probes for these uses may be conventionally designed and synthesized chemically or recombinantly [see, e.g., Merrifield, supra; Maniatis et al, supra].

One stage-specific subtraction library according to the invention was prepared from the 2CSL and was enriched for genes expressed at the 2-cell stage of embryogenesis. As described in more detail in Example 4 below, this library, designated 2CSL-I, has been successfully isolated and fourteen novel mammalian genes were identified from the first twenty cDNA clones investigated. Four of these twenty clones, or 20%, are expressed predominantly at the 2-cell stage, a value corresponding well with the estimates of 2-cell stage specific polypeptides following 2-dimensional gel electrophoresis analysis of the preimplantation mouse embryo [Latham et al, *Development*, 112:921–932 (1991)]. Also provided is a second library enriched for genes expressed at the 2-cell stage of embryogenesis, designated 2CSL-II.

The above-discussed subtractive libraries were deposited for patent purposes at the ATCC and the 2CSL-I has ATCC #69025, and was deposited on Jun. 30, 1992; and the 2CSL-II has ATCC #69023, and was deposited on Jun. 30, 1992.

The following examples illustrate the preferred methods for preparing the libraries and clones of the invention. These examples are illustrative only and do not limit the scope of the invention.

EXAMPLE 1
Library and insert size of egg and embryonic cDNA libraries

A single mouse embryo at any stage of preimplantation development contains no more than 50 pg of poly $(A)^+$ mRNA [K. B. Clegg et al, *Dev. Biol.*, 95:331–341 (1983)]. Therefore a cDNA cloning strategy was optimized to permit efficient library construction using from 10–100 ng mRNA, as described below. Plasmid vectors, which can accommodate the directional cloning of cDNA, were employed so that T7 and T3 RNA polymerase promoter sequences could be used to generate "sense" and "anti-sense" transcripts for subtractive hybridization.

Libraries of $1–2 \times 10^6$ clones were obtained from the 50–175 ng of poly $(A)^+$ isolated from unfertilized eggs, 2-cell, 8-cell and blastocyst.

A. Mice and embryo recovery

Unfertilized eggs, 2-cell, 8-cell and blastocysts embryos were collected from 6–8 week old B6D2/F$_1$ mice (Jackson Laboratories, Bar Harbor, Me. or Harlan-Spague Dawley, Indianapolis, Ind.) after superovulation [B. Hogan et al, "Manipulating the Mouse Embryo", Cold Spring Harbor Press, Cold Spring Harbor (1986)] and mated to B6D2 male mice. Unfertilized eggs were treated with hyaluronidase and subsequently with pronase, while cleavage stage embryos and blastocysts were treated with Pronase alone [B. Hogan et al, cited above]. Eggs and embryos from all stages were repeatedly washed in modified Whitten's medium [J. Abramczuk et al, *Dev. Bio.*, 61:738–783 (1977)] and pools of 500–1000 were placed in embryo lysis buffer (ELB; 100 mM NaCl, 50 mM Tris-HCl pH 7.5, 5 mM EDTA, 0.5% SDS, 100 µg *E. coli* tRNA, Boehringer Mannheim), which had been preincubated with 0.5 mg/ml proteinase K (Boehringer Mannheim) for 30 minutes at 37° C. to remove any contaminating RNAse. Two cell stage embryos were harvested at 40–42 hours post-hCG, 8-cell stage at 68–70 hours and blastocyst stage at 92–95 hours and similarly treated. It is recommended that the RNA from embryos be extracted and purified immediately following embryo isolation to ensure a high yield of intact RNA; essential for the synthesis of quality cDNA.

B. Embryo RNA isolation

The embryo/ELB solution was incubated for 1 hour at 37° C., extracted twice with phenol/chloroform, and nucleic acids collected by ethanol precipitation and stored at −70° C. in absolute ethanol [J. Sambrook et al, cited above]. Aliquots of embryo RNA were removed and microcentrifuged for 60 minutes. The 70% ethanol washed pellet was air dried, redissolved in 80 µl of RNAse-free water and 20 µl 5×DNAse buffer (250 mM Tris-HCl pH 7.5, 1M NaCl, 50 mM MgCl$_2$, 25 mM CaCl$_2$), 1.5 mg DNAse-I [Worthington Biochemicals, preincubated at 37° C. for 30 minutes with 0.5 mg/ml proteinase K (Boehringer Mannheim) to remove contaminating RNAse], was added (37° C. for 30 minutes). DNAse digestion was terminated by adding 10 µl 0.25M CDTA, 5 µl 10% SDS and 2 µl proteinase K (20 mg/ml) followed by incubation at 56° C. for 15 minutes. The solution was extracted twice with phenol/chloroform and the total embryonic RNA was ethanol precipitated as before.

Poly $(A)^+$ mRNA was selected using poly-(dU) Sephadex according to the manufacturer's protocol (GIBCO/BRL). Briefly, 20–50 mg poly-(dU) Sephadex beads were resuspended in 1 ml NTS (20 mM Tris-HCl pH 7.5, 1 mM EDTA, 0.2% SDS, 0.4M NaCl) in a 1.5 ml microcentrifuge tube, swollen and then spun briefly to the pellet beads. The beads were washed 3× with 1 ml NTS and then an equal volume of NTS was added to the packed beads. The DNAse-treated total embryonic RNAs were pelleted and resuspended in 20–25 ml RNAse-free H$_2$O and RNA aliquots from a given stage were pooled and added to an equal volume of 2×NTS, mixed, added to the prewashed poly (dU) Sephadex beads and lightly agitated for 10–20 minutes. Unbound RNA was removed by three 1 ml NTS washes followed each time by a brief spin to pellet beads. Nonspecifically bound RNA was further washed with a low-salt NTS (NTS with 0.1M NaCl) as described above. Bound poly $(A)^+$ was eluted from the beads by addition of 50 µl EL (0.1% SDS, 20 mM Tris-HCl pH 7.5, 1 mM EDTA, 90% deionized formamide) followed by incubation at room temperature (RT) with gentle agitation for 10 minutes. After a 30 second spin in the microfuge to pellet beads, the supernatant was transferred to a tube containing 200 µl chloroform and 5 µg tRNA carrier, extracted and the aqueous phase recovered. Two volumes of ethanol were added and after −70° C. incubation for several hours, RNA was pelleted by centrifugation for 60 minutes. After washing with 70% ethanol the pellet was air dried, resuspended in 8.3 ml RNase-free water and stored at −70° C.

C. RNA quantification

RNA was quantified by visually comparing the amount of ribosomes present in each sample as determined by Northern blot analysis [J. Sambrook et al, cited above]. Serial dilutions of standard RNA from a mouse epithelial cell line was run on the same gel as embryonic RNA. The amount of total embryonic RNA was estimated based on visual comparison of ribosomal band intensities of standard RNAs to those of embryo RNAs after hybridization with a random-primed $^{32}$P-dCTP labeled 28/18S ribosomal probe [James Sylvester, University of Pennsylvania]. Any aliquots of RNA that showed degradation were discarded; all other RNA of identical embryonic origin were pooled and stored either in RNAse-free H$_2$O or as a pellet under 70% ethanol at −70° C. The level of poly $(A)^+$ mRNA was estimated at five percent of the total mRNA [L. Piko et al. *Dev. Biol.*, 89:362–378 (1982); and D. H. Giebelhaus et al, cited above].

Since a library of $10^6$ clones has a greater than 99% probability of including rare transcripts (less than 10 copies per cell) at a detectable frequency [J. Sambrook et al, "Molecular Cloning: A Laboratory Manual, Cold Spring Harbor Press, Cold Spring Harbor, N.Y. (1989)], these egg and embryonic stage libraries are likely to contain representatives of not only abundant but also of medium and low abundance transcripts in the egg or embryonic stage. Each of these four libraries contain at least $10^6$ clones (Table I). The total RNA values of the unfertilized egg and blastocyst stages in the following table are calculated based on values of Piko and Clegg, Dev. Biol., 89:362–378 (1982). The total RNA values of the 2-cell and 8-cell stages in the table were determined using northern analysis of 18/28S ribosomal RNA in the embryonic samples compared with ribosomal RNA from a standard amount of cellular RNA. The polyA estimates were based on 5% poly(a)$^+$RNA. Additionally the column labelled "Library Size" reflects the total number of clones plated on primary filters.

TABLE I

| Embryonic stage | Number Females | Number Embryos | RNA (ng) Total | (Poly A)$^+$ | Library Size (cfu) |
|---|---|---|---|---|---|
| Unfert. egg | 200 | 5000 | 1750 | 175 | $2 \times 10^6$ |
| 2-Cell | 665 | 13500 | 910 | 46 | $1 \times 10^6$ |
| 8-Cell | 300 | 2778 | 1740 | 87 | $2 \times 10^6$ |
| Blastocyst | 100 | 600 | 900 | 45 | $1 \times 10^6$ |

The insert size of 25–50 randomly-picked independent clones per library was determined by PCR as described in Example 2 below, using primers to the T3 and T7 promoter sites in the cloning vector. A representative gel of 11 clones from the 2 cell stage shows the average insert size is ≈950 bp. Overall, the average insert sizes are: unfertilized egg 1.0 kb; 2-cell stage 1.3 kb; 8-cell stage 0.7 kb; and blastocyst 1.0 kb. The modal size of an unfractionated population of mRNA molecules is estimated to be approximately 2 kb [Clegg and Piko, Devel. Biol., 95:331–341 (1983)], thus the chance of obtaining near full length cDNAs is quite high in the egg and embryonic libraries.

EXAMPLE 2
cDNA Library Construction
A. First strand and Second Strand Synthesis

First and second strand cDNA synthesis was performed by modification of the method described in U. Gubler et al, Gene, 25:263–269 (1983). Since the first strand of cDNA determines the length and quantity of cDNA in the final library, the conditions for first strand synthesis were optimized using a 7.5 kb synthetic mRNA molecule. After analyzing several first strand buffers and reverse transcriptase enzymes, the conditions for optimal length and quantity of first strand cDNA were found that allowed the synthesis of cDNA from as little as 10 ng of input mRNA. The addition of 5 µg/reaction of E. coli tRNA improved the recovery of full length cDNA by approximately 2–5 fold. The addition of glycogen (5 µg per reaction) was inhibitory to first strand synthesis and resulted in a reduced yield of full length first strand product. Given a constant concentration of reaction components, the volume of the first strand reaction did not dramatically effect the efficiency of the reaction; however, consistent results were obtained in a total volume of 33 µl. In addition, oligo (dT) primer and oligo (dT)/Sal-I linker-primer were equally effective in priming first strand reactions. Thus, to simplify the procedure and increase directional cloning efficiency, first strand cDNA synthesis was performed using an oligo (dT)/SalI linker-primer as follows.

RNA in 8.3 µl of H$_2$O was heated to 65° C. for 15 minutes to remove secondary structure and placed immediately on ice. All first strand reactions were assembled on ice in a total volume of 33 µl. For each reaction contained 6.6 µl of 5×reverse transcriptase buffer (GIBCO/BRL), 3.3 µl 10 mM dNTP's (Pharmacia), 500 ng oligo(dT)/Sal-I linker primer [SEQ ID NO: 1] [5'pCGGTCGACCGTCGACCG(T)$_{15}$3'], 1.3 µl bovine serum albumin (BSA, Boehringer Mannheim, 2.4 mg/ml), 1 unit of human placental RNAse inhibitor (Boehringer Mannheim), 50 µCi $^{32}$P-dCTP (3000 mCi/mM, Amersham) and 200 units Superscript™ RNAse H$^-$ MMLV reverse transcriptase (GIBCO/BRL) was added to denatured RNA and incubated at 37° C. for 60 minutes. The amount of RNA converted to cDNA was quantified as described in J. Sambrook et al, cited above, on nylon membrane using 3 µl sample of the first strand reaction (1 µl total cpm, 1 µl incorporated and 1 µl used for background determination prior to first strand synthesis) and using standard amounts of cellular mRNA, was consistently 30±8%. Second strand synthesis was performed in the same tube in a total volume of 200 µl.

After determining the amount of incorporated cDNA, the remaining 30 µl first strand reaction, 20 µl 10×second strand buffer [J. Sambrook et al, cited above], 2 units RNAse-H (Pharmacia), 70 units DNA polymerase-I holoenzyme (Boehringer Mannheim), 20 µl dNTP's (10 mM each) and sterile, nuclease-free H$_2$O q.s. 200 µl were incubated at 15° C. for 1 hour followed by 1 hour at room temperature (RT). The reaction was terminated by addition of 2.5 µl 0.25M EDTA, 5 µl glycogen (1 mg/ml, Boehringer Mannheim), 7 µl 10% SDS, and 50 µg proteinase K, and incubation, 56° C. for 15 minutes.

B. S$_1$-nuclease and end repair

For all cDNA synthesis reactions, S$_1$-nuclease was used to increase the amount of clonable cDNA.

Following phenol/chloroform extraction, addition of an equal volume of 5M NH$_4$OAc, and ethanol precipitation, S$_1$-nuclease treatment of double stranded cDNA was performed [U. Gubler et al, cited above] in a total volume of 100 µl using 200 units of S$_1$-nuclease (Boehringer Mannheim) in 1×S$_1$ buffer (0.1M NaOAc, 0.8M NaCl, 2 mM ZnCl$_2$) at 37° C. for 20 minutes. The amount of Sl-nuclease that degraded the ends of the digested DNA fragments as determined by smearing of low molecular weight fragments on a 1.2% agarose gel was chosen for use in cDNA synthesis. Following S$_1$ treatment, nuclease reactions were terminated by adding 20 mM Tris-HCl pH 8.3, phenol extracted, and ethanol precipitated as before except for the addition of 20 mM Tris-HCl pH 8.3. Nuclease-treated cDNA was end-repaired by resuspension in 11 µl nuclease-free H$_2$O, 4 µl 5×T4-polymerase buffer (0.2 M Tris-HCl pH 7.5, 50 mM MgCl$_2$, 10 mM EDTA, 40 mM DTT, 1 mg/ml BSA), 4 µl dNTP's (10 mM each), 1 unit of T4-polymerase (Boehringer-Mannheim) and incubation at 37° C. for 15 minutes [J. Sambrook et al. cited above]. End-repaired cDNA was phenol/chloroform extracted and ethanol precipitated.

C. 5' linker ligation and double digestion

5'-phosphorylated Mlu-I linkers (3 μg, Pharmacia LKB Biotechnology) were ligated to blunt-ended cDNA using 1 Weiss unit of T4 ligase (GIBCO/BRL) in 30 μl at 15° C. for 16–18 hours [J. Sambrook et al, cited above] in ligase buffer (20 mM Tris-HCl, pH 7.2, 10 mM $MgCl_2$, 0.2 mM rATP). After incubation, ligase was inactivated at 65° C. for 10 minutes and the cDNA was doubly digested with the restriction enzymes Sal I and Mlu I (New England Biolabs) in a total volume of 400 μl for 5–6 hours at 37° C., using conditions suggested by the manufacturer. Digestion reactions were terminated, phenol/chloroform extracted and ethanol precipitated as described above. T4 ligase from GIBCO/BRL provided the highest efficiency of ligation.

D. Size fractionation and vector ligation

Double digested cDNA was resuspended in 15 μl of nuclease-free $H_2O$, 10 μl saturated urea, 1 μl bromphenol blue tracer dye (1 mg/ml) and loaded onto a 1 ml Sepharose CL4B column (Pharmacia LKB Biotechnology) which had been prewashed in column buffer (20 mM Tris-HCl, pH 7.5, 0.2M NaOAc, 4 mM EDTA, 0.1% SDS).

The cDNA was loaded onto the column bed and fractions of 100–200 μl were collected. cDNA greater than 500 bp were eluted in the first radioactive peak, whereas the second peak contained smaller cDNAs and unincorporated nucleotides. The elution of cDNA molecules was monitored using a hand-held Geiger counter which will distinguish the two major radioactive peaks. The first peak contains the cDNAs greater than 500 bp, whereas the second peak contains smaller cDNAs and unincorporated nucleotides. Precipitated cDNA was resuspended in water at a concentration of 0.25–1 ng/ml and ligated into an excess of linearized pBS™ vector (Stratagene) for 18 hours at 15° C., modified so that the EcoRI site was converted to an Mlu I site and HindIII site converted to a Sal I site. Single fractions were Cherenkov counted to determine the quantity of cDNA in each fraction. If enough cDNA is available (2000 cpm represents <5% of the total pooled radioactivity) samples were examined on an alkaline agarose gel. Fractions containing cDNA with an average size greater than 500 bp were pooled and ethanol precipitated with the addition of 5 ug glycogen.

The yield of cDNA from the column was determined for the egg and embryonic stages and varied from 28 to 63% of the starting cDNA loaded onto the column (Table II). Precipitated cDNA was resuspended in water at a concentration of 0.25–1 ng/μl and ligated into an excess of linearized pBSTY vector (Stratagene) modified so that the EcoRI site was converted to MluI and HindIII site converted to SalI.

The purification of digested vector is critical to the frequency of cDNA containing clones in the final library. The vector is propagated with a "stuffer" sequence that is large enough to allow efficient enzyme digestion while not being too close to the size of the vector itself. Generally, a stuffer of 500 bp is used. The vector is digested overnight and purified from stuffer in no less than 2 vertical agarose gels. The background (vector ligated without cDNA insert) is no greater than $1\times10^6$ cfu/μg of vector when the electroporation efficiency is $2\times10^{10}$ for supercoiled plasmid.

TABLE II

Efficiency of Embryonic cDNA cloning

| Stage of cDNA library | Poly(A)+ RNA (ng isolated) | ng of ds cDNA Synthesized | Yield (%) | # clones | Efficiency (cfu/μg) |
|---|---|---|---|---|---|
| Unfert. egg | 175 | 53 | 15 (28) | $2\times10^6$ | $1.3\times10^8$ |
| 2-cell | 46 | 14 | 7 (53) | $1\times10^6$ | $1.4\times10^8$ |
| 8-cell | 87 | 26 | 16 (63) | $2\times10^6$ | $1.3\times10^8$ |
| Blastocyst | 45 | 14 | 5 (38) | $1\times10^6$ | $2.0\times10^8$ |

In the above table, Poly(A)+ RNA was calculated based on the percent conversion of mRNA to double stranded (ds) cDNA=30±8%; the ng of ds cDNA synthesized was determined by the amount of $^{32}$P-dCTP incorporation into first strand cDNA; yield of ds cDNA was based on recovery of $^{32}$P-dCTP labeled cDNA>500 bp from Sepharose CL4B column; the number of clones refers to the number of independent clones plated; and efficiency is based upon the clones/μg of cDNA recovered from Sepharose CL4B column.

E. Bacterial electroporation and plating

Following incubation, ligation reactions were phenol/chloroform extracted, ethanol precipitated and resuspended in 10 μl TE (10 mM Tris-HCl pH 7.5, 0.1 mM EDTA) prior to bacterial electroporation.

The E. coli strain DH10B (GIBCO/BRL) used for electroporation was grown and made electrocompetent as described in Hanahan et al, Methods Enzymol., 204:63–112 (1991). All electroporations were performed using a Cell Porator™ (GIBCO/BRL) set at 400 volts and 4000Ω, resulting in line voltages of 2.4–2.5 KV. Electrotransformation efficiencies of $3-6\times10^{10}$ cfu/μg plasmid were routinely obtained with the control, 10 pg pUC19 (Pharmacia, Uppsala, Sweden).

Electroporation of cDNA libraries resulted in transformation efficiencies of $2-3\times10^8$ cfu/ng cDNA. Bacteria were electroporated with cDNA in 1 ml of TE, grown in SOC medium [Hanahan et al, cited above] at 37° C. for 60 minutes, pooled and spun at 400×g for 10 minutes. Cell pellets for each library were resuspended in 1 ml SOC for every 250,000 estimated transformants and each 1 mL plated onto 8.5×8.5 inch MSI nylon membranes placed on top of LB agar plates (Nuncleon) containing 70 μg/mL ampicillin (LB/amp) [Sambrook et al, cited above] and incubated overnight, 37° C.

The following day filters were replica plated as follows. The master filter was removed from the agar surface and placed, colony side up, on 3 mm blotting paper dampened with LB/amp medium. The first replica filter was then placed on top of the master followed by another piece of dampened 3 mm blotting paper. Firm pressure was applied using a glass plate for one minute then removed, 10–15 orientation marks placed using a 18 g needle and the two filters separated and placed onto agar plates to incubate at 37° C. for 2–3 hours. The second and third replicas were made from the master in the same fashion. The replica filters were grown at 25° C. for 3–4 hours or until colony sizes were similar to those of the master. The third replica was grown overnight at RT and scraped with Hogness Modified Freezing Medium (HMFM) diluted in LB/amp and aliquoted and stored at –70° C. The master filter was soaked on HMFM, placed on a plastic sheet (8.5×8.5×⅛ inch), covered with a transparency of a standard graph paper, followed by another plastic sheet and stored at −70° C. A copy of the transparency containing the orientation marks was made and kept in a notebook for later orientation of autoradiographs. The replica filters were denatured, neutralized, baked and UV treated as described in Sambrook et al, cited above. All hybridizations were performed using both replicas to authenticate colony hybridization with specific probes.

F. General Screening

To determine whether the library inserts represent authentic mRNAs, each library was screened for the presence of cDNAs representative of 28S/18S ribosomal RNA as follows. Only colonies hybridizing with a given probe on two replicated library filters were considered positive. Subsequent secondary screening was performed on smaller library aliquots to verify positive signals and to isolate clones for sequencing. The frequency of a given transcript in a library was determined by calculating the number of positive colonies per the total cDNA colonies screened.

All probes used for hybridization were $^{32}$P-dCTP labeled using the primer extension method [Feinberg and Vogelstein, Analyt. Biochem., 132:6 (1983)] and 1–2×10$^6$ cpm/ml hybridized to nylon filters in Church buffer (7% SDS, 1 mM EDTA, 0.5M sodium phosphate, pH 7.2) at 65° C. for 18–20 hours. Filters were washed the following day in Church wash (1% SDS, 50 mM sodium phosphate buffer, pH 7.2) followed by (high stringency wash (0.1×SSC, 50 mM sodium phosphate buffer, pH 7.2). Probes for known genes such as 28S/18S ribosomal, cytochrome-c oxidase I and II, β-actin, intracisternal A-type particle (IAP), tissue plasminogen activator (t-PA), and B1/B2 repeats were used to screen library filters generated by replica plating to determine cDNA library quality and representation.

The probes used for hybridization were pTAM [(Full length t-PA cDNA); S. Strictland (SUNY, Stony Brook)], [Rickels et al, J. Biol. Chem., 263:1563–1569 (1988)] 28/18S rRNA, mitochondrial cytochrome-c oxidase I and II cDNA clone [L. Piko et al, Dev. Biol., 123:364–374 (1981)] and the murine β-actin cDNA clone which was isolated from the mouse 8-cell library using a chicken β-actin cDNA as described in S. Alonso et al, J. Mol. Evol., 23:11–22 (1986).

Radioactive probes were obtained by isolating inserts from plasmids by appropriate restriction enzyme digestion, agarose gel purification, and labeling using the random primer method [A. P. Feinberg et al, cited above]. They were hybridized to library filters (1–2×10$^6$ cpm/ml) in Church buffer (7% SDS, 1 mM EDTA, 0.5M sodium phosphate buffer pH 7.2), 65° C. for 18–20 hours.

To determine whether these libraries contained clones representative of genes known to be expressed at these stages of development, they were probed with a mouse β-actin cDNA probe. Between 200 and 355 of the 250,000 clones screened in each library hybridized with the β-actin probe (Table III). These values, when converted to a per embryo basis (see part A above), indicate that 18,700 actin mRNA molecules are present and 5,600 in the late 2-cell stage. These values correspond well to previous reports of total (β and γ) actin in the egg and 2-cell stages, i.e. 21,000 copies of actin mRNA in the egg, 3700 in the 2-cell stage by Taylor and Piko, Mol. Repro. Dev., 26:111–121 (1990), are close to those of R. Bachvarova et al, Dev., 106:561–565 (1989). However, an increase in the number of actin transcripts in the 8-cell stage (18,460) and blastocyst stages (41,480) was observed, a pattern similar to previous reports [Taylor and Piko, cited above]. The levels of actin in the libraries corroborate those of Taylor and Piko and Bachvorova et al, both cited above and are substantially lower than the figures from comparable stages previously reported [Giebelhaus et al, Devel. Biol., 98:148–154 (1983) and Giebelhaus et al, Devel. Biol., 107:407–413 (1985)].

In addition, the abundance of mitochondria-encoded cytochrome-c oxidase I and II was examined to determine the level of contamination with mitochondrial messages. Very few to no detectable clones were identified that hybridized to these probes (Table III) suggesting that the preimplantation libraries contain greater than 99% poly (A)$^+$ mRNA from cytoplasmic sources.

TABLE III

| cDNA Library | Probes | | |
|---|---|---|---|
| | 28/18S rRNA | Cyctochrome-c oxidase | β-Actin |
| Unfert. Egg | 0 (0.000)* | 0 (0.000) | 275 (0.110) |
| 2-cell | 0 (0.000) | 20 (0.008) | 200 (0.080) |
| 8-cell | 1 (0.0004) | 0 (0.000) | 355 (0.270) |
| Blastocyst | 0 (0.000) | 0 (0.000) | 305 (0.610) |

*Number of positive of 250,000 colonies (percent expression per embryo; determined by normalizing the number of cDNA clones in each stage-specific library to the number of poly(A)$^+$ mRNAs sampled per embryo).

Since the cDNA libraries are derived from poly (A)$^+$ RNA, the variability associated with comparisons of actin expression in total embryonic RNA and standards derived from total cellular RNA is avoided [see, K. D. Taylor et al, cited above]. Thus, the actual level of poly (A)$^+$ containing β-actin transcripts in the egg and preimplantation stages of development is accurately reflected in the direct analysis reported here. Transcripts of tissue-type plasminogen activator (t-PA) have previously been shown to decrease in maturing oocytes until they become nearly undetectable at ovulation [J. Huarte et al, Cell, 43:551–558 (1985); J. Huarte et al, Genes Dev., 1:1201–1211 (1987); S. Strickland et al, Science, 241:680–684 (1988)]. Indeed, expression of t-PA in the unfertilized egg has been estimated at less than or equal to 0.05% of total RNA [J. Huarte et al, cited above].

Colonies screening positive for a probe on two replicated filters are considered positive. Expression values for a given gene were determined and the number of positive colonies/ 250,000 screened. The predicted number of transcripts of a given gene per embryo was calculated by multiplying the frequency of its occurrence in the cDNA library by the total number of poly (A)$^+$ RNAs at each corresponding stage.

To determine the representation of t-PA in the unfertilized ovulated egg library, a mouse t-PA cDNA clone was hybridized [R. J. Rickles et al, J. Biol. Chem., 263:1563–1569 (1988)] to replica filters containing 250,000 clones. It was found that 60 clones hybridized in the egg library, representing 0.024% of the transcripts in the mouse egg (Table IV).

TABLE IV

Representativeness of gene expression in cDNA libraries

| cDNA Library | Probes* | | | |
|---|---|---|---|---|
| | | | Repetitive Elements | |
| | t-PA | IAP | B1 | B2 |
| Unfert. egg | 60(.024) | 88(.035) | 26(0.130) | 30(0.150) |
| 2-cell | 0 | 275(.110) | 404(2.020) | 725(3.625) |
| 8-cell | 0 | 53(.021) | 150(0.750) | 100(0.500) |
| Blastocyst | 0 | 2(.001) | 4(0.020) | 50(0.250) |

Table IV above lists the number of positive clones when the probes pTAM, clone 11 (genomic clone containing the 5' LTR and coding regions of a mouse IAP gene) and IAP-H were used to screen 250,000 colonies or pB1/B2 were used to screen 20,000 colonies. Clone 11, described in Piko et al, *Proc. Natl. Acad. Sci. USA*, 81:488–492 (1984), was kindly provided by L. Piko, Veterans Administration Hospital, Sepluveda, Calif. Murine B1/B2 cDNA probe [Z. Larin et al, *Proc. Natl. Acad. Sci. USA*, 88:4123–4127 (1991)] was provided by M. Bucan (University of Pennsylvania, Philadelphia).

Three representative t-PA clones were partially sequenced from the 3' end and found to be homologous to the 3' untranslated region of the mouse t-PA gene cloned from the F9 teratocarcinoma-derived cell line [R. J. Rickles et al, cited above].

As expected no t-PA cDNAs could be detected in the 2-cell, 8-cell or blastocyst stage library (0/250,000 clones screened). Thus, the limited amount of t-PA transcription in these libraries is qualitatively, and quantitatively, consistent with previous information regarding transcription of this gene product.

The levels of highly expressed transcripts such as those of the intracisternal A-type particles [IAP, K. K. Lueders et al, *Proc. Natl. Acad. Sci. USA*, 77:3571–3575 (1980); J. A. Mietz et al, *J. Virol.*, 61:3020–3029 (1987)] and B1/B2 repeat sequences [D. A. Kramerov et al, *Nucleic Acids Res.*, 6:697–713 (1979); A. S. Krayev et al, *Nucleic Acids Res.*, 8:1201–1215 (1980)] have been previously analyzed in total embryo-isolated RNA [L. Piko et al, *Proc. Natl. Acad. Sci. USA*, 81:488–492 (1984); K. D. Taylor et al, *Development*, 101:877–892 (1987), A. A. Poznanski et al, *Dev. Biol.*, 143:271–281 (1991)]. It was found that 0.035% of the transcripts in the egg library hybridized by an IAP probe [Piko et al, *Proc. Natl. Acad. Sci. USA*, 81:488–492 (1984)] or by calculation, 5,950 transcripts in the unfertilized egg, are IAP. Similarly, 0.11% of those in the 2-cell stage (est. 7,700 transcripts), 0.021% of the transcripts (2,730) in the 8-cell stage and 0.001% of the transcripts (272) in the blastocyst are IAP. These results are quantitatively comparable at the 2-cell (7,100 IAP mRNA molecules) and similar at the 8-cell stage (9,700 IAP mRNA molecules) to those previously reported [Piko et al, cited above]. IAP levels appear higher in the egg and lower than those reported in the blastocyst, i.e. 1,300 mRNA molecules in the mouse egg and 37,900 mRNA molecules in the early blastocyst were estimated to be IAP [Piko et al, cited above]. The differences between the levels of IAP expression in blastocyst to those previously reported may reflect the known variation in IAP expression between mouse strains [E. Kuff et al, *Mol. Cell Biol.*, 5:474–483 (1985)] or the high percentage of nonadenylated IAP mRNA in the mouse blastocyst [Piko et al, cited above] which would not be represented in the blastocyst cDNA library.

B1 and B2 repeat sequences are abundantly expressed in the preimplantation embryo [Taylor and Piko, (1987), cited above]. These repeat sequences are found in the 5' or 3' untranslated regions of RNA polymerase II-generated transcripts and also as separate smaller ($\leq$500 bp) poly (A)$^+$ RNA polymerase III-dependent transcripts of unknown function [D. A. Kramerov et al, cited above; A. S. Krayev et al, cited above; and D. Murphy et al, *Cell*, 35:865–871 (1983)]. The abundance of these transcripts increased dramatically in these libraries at the 2-cell stage (Table IV), rising from about 0.1–0.2% of the clones detected in the unfertilized egg to 2–4% of the clones detected in the 2-cell stage, values that are quantitatively similar to those previously reported [Taylor and Piko, (1987), cited above, and Vasseur et al, *EMBO J.*, 4:1749–1753 (1985)]. Following this initial increase, the level of the B1 and B2 transcripts decreases in the 8-cell and blastocyst libraries, a result at odds with those in the literature.

Although the levels of B1 and B2 transcripts in the egg and 2-cell stage are quantitatively similar to those previously reported, there is a reduction in B1 and B2 expression in the 8-cell and blastocyst stage (Table III). Since the cDNAs used for library construction are derived from poly (A)$^+$ RNA and also have been size-selected, these results cannot be directly compared with those previously reported. Size selection would exclude smaller B1 and B2 ($\leq$500 bp) transcripts from these libraries; indeed, additional B1 sequences were found in the cDNA size cuts smaller than 500 bp. From this analysis of β-actin, t-PA, IAP, and B1/B2-repeats, genes known to be expressed in the egg and preimplantation embryonic stages, it has been concluded that these cDNA libraries represent the transcripts present in the corresponding stages in vivo. Thus, the libraries provide an in vitro source of genes transcribed at these stages of development.

The total numbers of mRNAs for the unfertilized egg, 2-cell, 8-cell and early blastocyst stages are, $1.4 \times 10^7$, $7 \times 10^6$, $1.3 \times 10^7$ and $3.6 \times 10^7$ mRNA molecules, respectively [Clegg and Piko, *Devel. Biol.*, 95:331 (1983).

G. PCR analysis of random cDNAs

Aliquots of each cDNA library were diluted and plated on small (100 mm) LB/amp plates to obtain 50–200 single colonies. Individual colonies were randomly picked from each library using a sterile pipette tip and placed into 30 µl of PCR buffer (10 mM Tris-HCl pH 8.3, 50 mM KCl, 2.5 mM MgCl2, 0.1 mg/ml gelatin, 0.45 NP40, 0.45% Tween 20) and denatured at 100° C. for 15 minutes followed by the addition of 20 IL-1 PCR mix (5' T7 primer 0.25 µg, 3' T3 primer 0.25 ug, 0.5 mM dNTPs, 2 units ThermalaseTM), placed in a thermal cycler for 35–45 cycles of 94° C. for 30 seconds, 50° C. for 30 seconds, and 72° C. for 1.5 minutes and products resolved on a 1.5–2.0% agarose gel. Primers for T7 and T3 polymerase promoters were synthesized using the same sequence as that published by Stratagene. The average insert size of each cDNA library was determined using this random PCR approach. The analysis of each library consisted of no less than 50 independently isolated cDNA clones which demonstrated that the average insert size of the unfertilized egg, 2-cell, 8-cell and blastocyst cDNA libraries were 1.0, 1.3, 0.7, and 1.0 Kb, respectively.

H. Gene specific PCR analysis

To determine whether the embryonic cDNA libraries contained specific genes that may be important for early growth and differentiation, the cDNA libraries were subjected to PCR analysis using primer for several cytokines. Cytokines such as interleukins 1–7 are expressed in a lineage specific fashion in cells of the hematopoietic system. In addition, the expression of these genes is tightly regulated making them appropriate probes for the analysis genes potentially regulated in the egg and early embryo. For PCR analysis bacterial aliquots from each library were plated at high density ($2 \times 10^6$ cfu) on Nucleon 8.5×8.5 inch LB plates containing 70 mg/ml ampicillin. Plates were incubated at 37° C. for 16 hours and scraped into 50 ml centrifuge tubes, spun at 2500×g and plasmid DNA isolated by the standard alkaline lysis method [Birnboim and Doly, *Nucleic Acids Res.*,7:1513 (1979)], purified by CsCl gradient centrifugation (Sambrook et al, cited above) and digested using Mlu I and Sal I as described by the manufacturer (New England Biolabs). Insert cDNA was purified from vector sequences by gel electrophoresis and separated from agarose using spin columns. For each PCR reaction 10–50 ng of purified insert cDNA was used as the starting template.

Primers for T7 and T3 polymerase promoters were synthesized in-house using the sequence published by Stratagene. Briefly, DNA template was denatured at 100° C. for 15 minutes in 30 µl autoclaved 1×PCR buffer (10 mM Tris-HCl pH 8.3, 50 mM KCl, 2.5 mM MgCl$_2$, 0.1 mg/ml gelatin, 0.45% NP40, 0.45% Tween 20) followed by the addition of PCR mix (T7/T3 primer 0.1 µg/ml, 0.2 mM dNTPs, 2 units Thermalase™, IBI/Kodak) and placed in a thermal cycler for 35–45 cycles of 94° C. for 30 seconds, 50°

C. for 30 seconds, and 72° C. for 1.0 minute. PCR reactions for cytokine primers were performed as recommended by Clonetech. Following amplification PCR products were analyzed on 1–3% agarose gels and, when necessary, transferred onto nylon membrane [J. Sambrook et al. cited above], exposed to 1,200 J of UV light using a Stratalinker 2400™, and hybridized with appropriate probes.

As described in more detail in Example 3 below, several cytokine genes were shown to be expressed in a stage specific fashion. For example, IL-7 was expressed as a maternal transcript in the mouse egg since screening of the egg library has shown that 8/250,000 clones or 0.0003% hybridize with the mouse IL-7 probe. Since the mouse egg contains $1.4 \times 10^7$ poly (A)+ mRNA molecules, this suggests that 448 transcripts in the mouse egg are IL7. No expression of IT-7 was detected in the 8-cell or blastocyst libraries by PCR. These data were verified by direct reverse transcription PCR of mouse eggs. Although there appeared a very low signal of IL-7 in the 2-cell stage embryo, IL-7 was not detected in the 2-cell stage cDNA library. These data demonstrate the sensitivity of using this approach to detect very low level gene expression during early embryogenesis.

EXAMPLE 3
Detection of cytokines in the cDNA libraries

To investigate whether the interleukins 1α and 1β, 2, 3, 4, 5, 6, 7 or interferon-γ are transcribed during preimplantation embryogenesis, the cDNA libraries from the unfertilized egg, 8-cell and blastocyst stages were screened as described above in Example 2F. Pooled inserts from each cDNA library were subjected to a primary screening by PCR (Example 2G) and expression of those cytokines identified by this method was confirmed by directly screening the cDNA libraries with authenticated probes as described above (Example 2G). PCR primer-sets specific for mouse interleukins 1–7 and interferon-γ genes are commercially available from Clonetech Laboratories.

Insert cDNA was isolated by gel electrophoresis and 10–25 ng amplified by PCR using T7 and T3 oligonucleotide primers for 45 cycles (94° C., 30 seconds; 50° C., 30 seconds; 72° C., 1 minute). These results are illustrated in Table V below, in which "+" indicates the presence of a specific signal for the indicated cytokine by Southern hybridization. All cytokine-specific primers were tested in reverse transcriptase PCR reactions with total RNA derived from mouse peritoneal exudate and spleen cells and were shown to give the appropriate size bands on EtBr-stained agarose gels.

TABLE V

| Target gene | Embryonic Stage | | |
|---|---|---|---|
| | Egg | 8-cell | Blastocyst |
| IL-1α | – | – | – |
| IL-1β | – | – | + |
| IL-2 | – | – | – |
| IL-3 | – | – | – |
| IL-4 | – | – | – |
| IL-5 | – | – | – |
| IL-6 | – | + | + |
| IL-7 | + | – | – |
| IFN-γ | – | – | + |
| β$_2$M | + | + | + |

PCR analysis of the libraries showed IL-1β, IL6, IL-7, and IFN-γ to be expressed, but not IL-2, IL-3, IL-4, IL-5 (Table V). As expected beta-2 microglobulin [J. A. Sawicki et al, Nature, 294:450–451 (1981)] was present at all stages tested. Southern hybridization of the PCR gels using probes to IL-1β, IL-6, IL-7, IFN-γ and β$_2$M verified the presence of these transcripts in the libraries.

To quantify the level of cytokine expression in the embryonic libraries each stage was screened with a PCR-generated gene-specific probe. The murine IL-7 cDNA probe was kindly provided by S. Gillis and L. Park (Immunex). Screening 250,000 clones of each library with an IL-7 probe showed 8 positive clones expressed in the unfertilized egg library while no colony hybridization was seen with the same number of clones from 8-cell and blastocyst libraries. Thus, IL-7 transcripts appear to be rare in the mouse egg (0.003% of the independent cDNA clones in the library) and undetectable in the early embryo. Sequence analysis of two of the IL-7 hybridizing clones from the unfertilized egg library confirmed these to be 98% homologous to the mouse IL-7 gene [A. E. Namen et al, Nature, 333:571–573 (1988)]. IL-6, a mediator of the acute phase response [P. B. Sehgal, Proc. Soc. Exp. Biol. Med., 195:183–191 (1990); and T. Hirano et al, Immunol. Today, 11:443–449 (1990)], was previously shown to be expressed at the blastocyst stage [R. Murray et al, Mol. & Cell. Biol., 10:4953–4956 (1990)].

The present examples show that IL-6 is transcribed as early as the 8-cell stage persisting into the blastocyst stage (Table V). IL-1β, a pleiotropic cytokine expressed by multiple cell types with an important role in the inflammatory response [J. J. Oppenheim et al, Immunol. Today, 7:45–56 (1986); and C. A. Dinarello, Adv. Immun., 44:153–205 (1989)], is expressed by mammalian placental tissue and cultured trophoblast-derived cell lines [T. Taniguchi et al, Am. J. Obstet. Gynecol., 165:131–137 (1991)]. The function of IL-1β in the developing embryo is not known and there have been no reports of its synthesis during early embryonic development. Even though PCR analysis of IL-1β showed it to be expressed at the blastocyst stage, no hybridizing colonies in the $5 \times 10^5$ colonies screened were detected using a probe homologous to the 5' end of IL-1β.

Thus, the sensitivity of direct library screening is lower than that of PCR and it is estimated that 20 ng of cDNA insert was sampled by PCR, representative of the amount of cDNA in $4 \times 10^6$ clones and, therefore, twenty-fold more than the actual number of clones screened. These data suggest that IL-1β is either expressed as a rare message in each cell or by a small number of specialized cells in the mouse blastocyst or is actually present in the blastocyst library at a higher level but was not detected using the 5' IL-1β probe. Interferon-γ is also expressed in the mouse blastocyst (Table V), an observation that correlates with the observation that the mouse blastocyst secretes a factor conferring interferon-like anti-viral activity in vitro [J. C. Cross et al, Mol. Reprod. Devel., 26:122–128 (1990); and G. L. Nieder, Biol. Reprod., 43(2):251–259 (1990)]. A member of the α-interferon gene family was previously identified as one of the major proteins expressed by the bovine, ovine, caprine and porcine blastocysts. [K. Imakawa et al, Nature, 330:377–379 (1987); T. R. Hansen et al, J. Biol. Chem., 263:12801–12804 (1988); J. C. Cross et al, Bio. Reprod., 40:1109–1118 (1989); K. Imakawa et al, Mol. Endocrinol., 3:127–139 (1989); Roberts et al, J. Interferon Res., 9:175–187 (1989); and G. A. Baumbach et al, Biochem. Biophys. Res. Commun., 172:16–21 (1990)].

These data supply the first evidence for expression of any interferon in the murine blastocyst. By screening these libraries with probes of known cytokines, the transcription of genes whose products are often expressed in differentiated cell types and which themselves mediate a change in gene expression has been demonstrated.

EXAMPLE 4
Isolation of novel stage-specific genes by subtractive hybridization To identify genes whose expression changes during pre-implantation development, specialized libraries were generated by subtractive techniques. Directional cloning in the Bluescript™ vector [Stratagene] permitted the use of a modification of the biotin-streptavidin method [described previously by H. Sive et al, *Nucleic. Acids Res.*, 206:467–4491 (1988)] to obtain unique mRNA molecules. T7-promoted, "anti-sense" single-stranded and hybrid RNA molecules were separated from single-stranded T3-promoted, "sense" as described below and as shown in FIG. 1.

A. RNA transcription and subtractive hybridization

The template for "sense" RNA was generated by digesting cesium chloride-purified plasmid DNA with Sal I, 18 hours at 37° C., followed by treatment with 5 µg/ml proteinase K (Boehringer Mannheim) (56° C., 15 minutes) phenol/chloroform extraction and ethanol precipitation. Template for "anti-sense" RNA was prepared as above except that Mlu I was used instead of Sal I. RNA synthesis was performed using T7 or T3 RNA polymerase and the 5×reaction buffer supplied by the manufacturer (Promega). For a single transcription reaction 5–10 µg of template DNA was mixed with 1 mM each rATP, rGTP, rCTP and either rUTP or, for "anti-sense" RNA, biotin-UTP and rUTP together (10:1 respectively), and 100 units of polymerase in reaction buffer. Tracer, $^{32}$P-UTP was added at 1–2 µCi/reaction. Following incubation at 37° C. for 30 minutes, template was removed by DNAse treatment (1 mg/ml, 37° C. for 30 minutes), purified by phenol/chloroform extraction and ethanol precipitation. The amount of synthesized RNA was determined either spectrophotometrically or by calculating $^{32}$P-UTP incorporation as described above for first strand cDNA.

By this approach a 2-cell specific subtraction library was generated, hybridizing a 5-fold excess of biotinylated RNA from the egg library to that of the 2-cell library. The resulting 2-cell specific single-stranded RNA was separated from biotinylated RNA bound to streptavidin, then hybridized to a 10-fold excess of biotinylated-RNA from the 8-cell library. Following a second streptavidin treatment, the remaining single-stranded RNA was reverse-transcribed and cloned into plasmid vectors [Bluescript-11 SK+]. The average insert size of the cDNAs in the 2-cell subtraction library (2CSL-I) which contains 2×10$^6$ clones was 1.0 kb. The procedure described in FIG. 1, was repeated using the 2CSL-I library as the starting material resulting in a second 2-cell specific subtraction library (2CSL-II) of 2×10$^7$ clones which had an average insert size of 300–400 bp. The smaller size of the cDNAs in the 2CSL-II library is consistent with RNA degradation during the multiple and long incubation periods of double-stranded RNA hybrids at high temperatures.

To determine if these subtraction libraries are indeed reduced in complexity, both subtracted libraries were hybridized with probes to IAP, β-actin and B1/B2 repeat sequences as follows.

B. Subtractive hybridization

Although several methods exist to enrich for tissue or stage specific genes, a method was employed that takes advantage of the cRNA synthesis capabilities of the Bluescript™ plasmid cloning vector (Stratagene). A modified method of one described previously [Sive and St. John, *Nucleic Acids Res.*, 206:467 (1988)] uses the high affinity interaction between biotin and avidin as a means to separate biotinylated single stranded and hybrid RNA molecules containing the sense and antisense transcripts transcribed from two different stage cDNA libraries. To determine the efficiency of subtraction an initial control experiment was performed on two non-cross hybridizing cDNA clones (p17 and p44) randomly isolated from the blastocyst library. In first part of this experiment clone p17 (850 bp) was transcribed in the sense orientation in the presence of $^{32}$P-rUTP and the RNA hybridized to a 10-fold excess of p44 RNA transcribed in the antisense orientation in the presence of biotinylated-rUTP. This RNA mixture was treated with streptavidin and phenol/chloroform extracted to separate any hybrid RNA and biotinylated single stranded RNA from the $^{32}$P-rUTP labeled sense RNA. Table VI shows the result of this experiment demonstrating that little nonspecific hybridization occurs for dissimilar cDNA clones, whereas identical clones hybridized in a similar manner resulted in 90% hybridization. This experiment represents a single hybridization reaction and, in all cases, subtractive hybridization between stages was performed two or more times.

TABLE VI

| Subtractive Hybridization: Single cycle controls | | |
|---|---|---|
| RNA hybridization | cpm in | |
| combinations | Aqueous | Organic |
| p17 sense* vs. p44 antisense⁺ | 248,550 | 4,650 |
| p17 sense vs. p17 antisense⁺ | 12,150 | 106,200 |

*$^{32}$P-dCTP labeled sense RNA from p17 cDNA clone (830 bp), synthesized as described.
⁺Biotinylated antisense RNA from p17 or p44 cDNA clone (1400 bp), synthesized as described.

It is known from previous studies that the mouse embryonic genome is first activated at the 2-cell stage, which is the first stage for which subtractive hybridization can be used to identify 2-cell stage specific sequences by subtracting egg and 8-cell cDNAs. Thus by using subtractive hybridization in connection with the high efficiency directional cloning procedure described herein, a 2-cell stage specific subtraction library was generated as a mean to identify developmentally regulated genes expressed at the time when most of the maternal message has been degraded and the first set of poly (A)+ mRNAs are synthesized from the zygotic nucleus. For subtractive hybridization with total embryonic cDNA the ratio of sense and antisense RNA was chosen to be 5:1 for egg and 2-cell and 10:1 for 8-cell and 2-cell respectively.

Hybridization reactions between egg and 2-cell RNA were as described previously [H. Sive et al, cited above]. Briefly, 200 ng of 2-cell library-derived RNA was coprecipitated with 1 µg of biotinylated egg library-derived RNA, then resuspended in 4.5 µl hybridization buffer (250 mM Hepes pH 7.5, 10 mM EDTA, 1% SDS) and 0.5 µl of 5M NaCl and hybridization was carried out (65° C., 48 hours) under oil. Then, 50 µl of 1×hybridization buffer without SDS was added followed by 5 µl streptavidin (1 mg/ml, GIBCO/BRL). The reaction mixture was incubated, 5 minutes RT, followed by phenol/chloroform extraction. The organic phase was extracted 2×with 25 µl of hybridization buffer without SDS and the aqueous phases were pooled, phenol/chloroform extracted three more times, ethanol precipitated and washed. The 2-cell library-derived "sense" RNA remaining after hybridization with egg library-derived RNA was hybridized to a 10-fold excess of 8-cell "anti-sense" RNA and treated as described above. The 2-cell library-derived "sense" RNA remaining after hybridization and phenol/chloroform subtraction was reverse transcribed and cloned into the pBS™ cloning vector (Stratagene) as described above.

The average insert size of the cDNAs cloned in the first 2-cell subtraction library (2CSL-I) was 1.0 kb. The 2CSL-I was further subtracted by repeating the procedure described in FIG. 1B by substituting 2CSL-I in place of the original 2-cell library. This second 2-cell specific subtraction library (2CSL-II) had an average insert size of 3–400 bp. The smaller size of the 2CSL-II library is a result of RNA degradation resulting from multiple and long incubation periods of double-stranded RNA hybrids at high temperatures. To determine if these subtraction libraries are indeed reduced in complexity, both libraries were hybridized with a probe to IAP, a gene whose transcripts are higher at the two cell stage than in either egg or 8-cell (Example 2F). Neither IAP-, nor β-actin-, nor B1/B2- containing cDNAs were detected in either subtraction library (250,000 clones screened).

D. Stage Specific Embryonic Clone Analysis

Since cDNAs in the 2CSL-I and -II libraries should be highly enriched for transcripts expressed in greatest abundance at the 2-cell stage of embryogenesis, twenty random clones of a size ≧500 bp in length are chosen for partial sequence analysis and compared to sequences listed in Genbank/EMBL databases. Clones are subsequently sequenced from both ends using Sequenase™ (USB) from the 5' end using the T7 primer and the 3' end using the T3 primer with [$^{35}$S]dATP as described by the manufacturer. Sequencing reactions are run on a 10% polyacrylamide, 6% urea gel at 2000 V for 6–8 hr and exposed to x-ray film overnight at −70° C. All sequences are compared to those listed in the Genbank/EMBL databases using the FASTA command of the UWGCG sequence analysis program [Devereaux et al, Nucleic Acids Res., 12:387 (1988)] and are expected to encode gene proteins of interest at the designated stage of embryonal development.

In addition, all clones were hybridized to the unsubtracted 2 cell cDNA library to determine expression levels at that stage of embryogenesis. Clones expressing at levels ≧0.0001% in the original 2-cell cDNA library were further analyzed for stage-specific expression by hybridization to the egg and 8-cell libraries allowing identification of 4 stage-specific cDNAs expressed predominantly or exclusively at the 2-cell stage of preimplantation development (Table VII). All four clones in the table below are novel.

TABLE VII

| Clone | cDNA Insert size (bp) | Positive Clones % Expression | | | Sequence Length (bp) |
|---|---|---|---|---|---|
| | | Egg | 2-Cell | 8-cell | |
| SSEC-3 | 500 | 3(0.001) | 10(0.004) | 0 | 320 |
| SSEC-C | 600 | 0 | 5(0.002) | 0 | 300 |
| SSEC-D | 600 | 75(0.030) | 400(0.160) | 10(0.004) | 382 |
| SSEC-P | 900 | 25(0.010) | 50(0.020) | 0 | 172 |

In the above table, the approximate size of the cDNA insert was based on agarose gel (φX 174 standard). The percent expression is based upon 250,000 clones of the library and the sequence information was obtained from combining partial 3' and 5' sequences of each clone. Nucleotide sequences are compared to those listed in Genbank/EMBL using "Wordsearch" and "FASTA" commands of the GCG software program [Devereux et al, Nucl. Acids Res., 12:387–395 (1984)]. The genes are found to be novel.

One cDNA sequence, SSEC-3 (Stage Specific embryonic clone) appears to be expressed predominantly at the 2 cell stage with a low level (0.001%) at the egg stage. Another sequence, SSEC-D, is a highly expressed message (0.16%) at the 2-cell stage approximately four-fold higher than in the egg. SSEC-C, is 2-cell specific cDNA, but is expressed at low levels. SSEC-P shows predominant expression in the 2-cell stage (0.02%), even though expression is observed at moderate levels (0.01%) in the egg, suggesting that this gene is either newly transcribed at the 2-cell stage or that its message is somehow protected during the generalized RNA degradation known to occur after fertilization [K. B. Clegg et al, cited above]. Each of these clones are authentic single copy mouse genes as determined by Southern analysis. SSEC-3, C, D, and P (4.0 kb) are small cDNAs. All of the remaining fourteen cDNAs were found to be of mouse origin, confirmed by Southern Blot hybridization, but were not detected in the 2-cell library after screening 250,000 clones and, therefore, are likely to represent extremely rare transcripts.

This approach has thus enabled the identification of novel cDNAs, probes for genes characterized by transcription changes during development. Moreover, it has been shown that isolation of novel cDNA clones of relatively rare transcripts from a specific embryonic stage is possible.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: unknown ( i i ) MOLECULE TYPE: DNA (genomic)

( x i ) SEQUENCE DESCRIPTION: SEQ ID NO:1:

CGGTCGACCG TCGACCGTTT TTTTTTTTT TT    3 2

What is claimed is:

1. Murine embryonic cDNA library constructed from unfertilized eggs ATCC #69022.

2. Murine embryonic cDNA library constructed from 2-cell stage preimplantation embryos ATCC #69027.

3. Murine embryonic cDNA library constructed from 8-cell stage preimplantation embryos ATCC #69024.

4. Murine embryonic cDNA library constructed from blastocyst-stage preimplantation embryos ATCC #69026.

5. Murine embryonic subtraction cDNA library designated 2CLS-I ATCC #69025.

6. Murine embryonic subtraction cDNA library designated 2CLS-II ATCC #69023.

7. A method for identifying a novel gene or gene fragment comprising the steps of:

synthesizing a DNA probe comprising a DNA sequence homologous to at least one DNA sequence within a murine embryonic cDNA library selected from the group consisting of UESL ATCC #69022, BSL ATCC #69026, 2CSL ATCC #69027, and 8CSL ATCC #69024, labeling the DNA probe, and hybridizing the labeled DNA probe to the selected library, said label permitting identification of the gene or gene fragment.

* * * * *